June 22, 1976
J. A. HERHOLDT
ROSE PLANT
Filed June 20, 1975
Plant Pat. 3,923
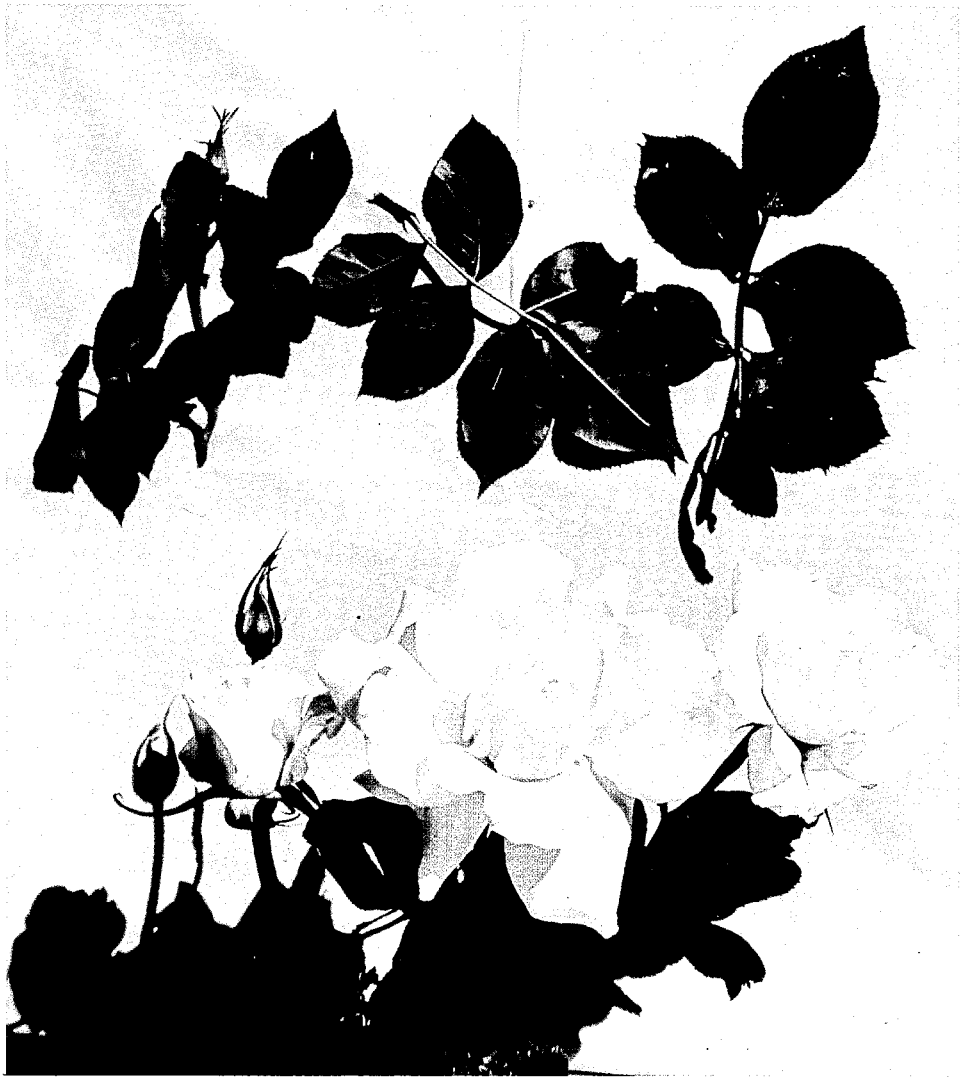

United States Patent

Plant Pat. 3,923

Patented June 22, 1976

3,923

ROSE PLANT

Jan Andries Herholdt, Roselandia, Eikenhof, Transvaal, Republic of South Africa

Filed June 20, 1975, Ser. No. 588,942

Int. Cl. A01h *5/00*

U.S. Cl. Plt.—14 1 Claim

The present invention relates to a new and distinct variety of rose plant of the hybrid tea class which was originated by me by crossing an unnamed hybrid tea seedling rose with a patented rose Pascali (U.S. Plant Pat. 2,592) of the hybrid tea class.

As a result of this crossing, I have produced a new and improved white rose variety which is distinguished from its parents, as well as from all other white hybrid tea varieties of which I am aware, as evidenced by the following description:

(1) The plant is of vigorous growth with an abundance of large glossy foliage which is resistant to disease.
(2) It is exceptionally free flowering and blooms from early spring until frost. A characteristic of the plant is that as soon as the flowers are formed, new flower shoots appear.
(3) The bud form is perfect, tightly formed, and opens perfectly in all weather conditions. The flowers are exceptionally large and double with 45 to 50 petals.
(4) The flowers are of a distinctive pure white colour—Horticultural Colour Chart plate 155D.

Asexual reproduction of the new variety by budding performed in various parts of the Republic of South Africa and under trial in France, Germany and Great Britain, proves that the foregoing characteristics and distinctions come true to form and are established and transmitted through succeeding propagations.

The accompanying transparency photos show typical specimens of the vegetative growths and flowers of my new variety in different stages of development and as depicted in colour as nearly true as it is reasonably possible to make the same colour illustration of its character.

The following is a detailed description of the new variety, with colour terminology in accordance with the Horticultural Colour Chart of the Royal Horticultural Society:

Type: It belongs to the hybrid tea class, for outdoor garden decoration.
Breeding: A seedling obtained by hybridising:
  Seed parent: An unnamed seedling of White Swan × an unnamed seedling.
  Pollen parent: Pascali.
Propagation: Holds its distinguishing characteristics through propagations by budding.
The place where the new rose was bred, tested and selected: The crossings out of which the new rose originated were made at "Heil-en-Lof," Eikenhof, in the Vereeniging District, Transvaal Province, Republic of South Africa, where the seeds which formed, were planted. The seedlings were planted on my farm "Bosfontein," Maanhaarrand, in the Rustenburg District, Transvaal, and when the young plants produced flowers, undesired plants were eliminated until the new rose here described was selected which answered to the object sought after.
Name of the new rose: Betty Herholdt.

FLOWER

Locality where grown and observed for the describing specifications: "Roselandia," Eikenhof, Transvaal Province, Republic of South Africa.

Colour: Ivory to snow white—Plate 155D.
Class: Hybrid tea.
Bud:
  *Form:* Perfect and well shaped, firm and with a high pointed centre.
  *Length:* When fully developed, 2½ to 2¾ inches long.
  *Peduncle:* Normally 3 inches long, stiff, strong, and of green colour, Plate 130, between A and B of the Royal Hortcultural Chart.
Flowering: Free flowering from spring until frost.
Bloom:
  *Size:* When fully open, 5 to 6 inches in diameter.
  *Opening:* The flowers open well under all weather conditions.
  *Petalage:* Very double—from 45 to 50 petals arranged regularly. The edges are curled backwards.
  *Petals:*
    *Texture:* Thick and firm.
    *Shape:* Ovate, and outer petal edges roll back.
    *Size:* Outer petals: 2¾ inches long and 2½ inches wide. Intermediate petals: 2½ inches long and 2 inches wide.
      Inner petals: 1½ inches long and 1⅝ inches wide.
    *Lasting:* (a) The flower lasts well on the plant from opening of bud—6 to 8 days and longer.
      (b) When cut under normal room temperature in water—5 to 6 days.
    *Flowers borne:* Singly to a stem, but sometimes also 2 and 3 flowers on one stem.
    *Flower stems:* Sturdy and stiff from 12 inches to 18 inches long and with few thorns.
    *Colour:* Green, Plate 132A.
    *Perfume:* The flowers have a soft sweet fragrance.

REPRODUCTIVE ORGANS

Stamens: Many, arranged about the pistils, a few mixed with petaloids.
Filaments: Medium in length, 5/16 inch to 7/16 inch in length, most with anthers and thin.
  *Colour:* Creamy-white—near Plate 158B.
Anthers: Medium size.
  *Colour:* Creamy, Plate 12D.
Pollen: Sparse to moderate.
  *Colour:* Yellow, Plate 12B.
Pistils: Average—number 55.
Styles: 3/16" to 5/16" in length, medium caliper, bunched, some mixed with petaloids.
  *Colour:* Pink, Plate 50 near B.
Stigma:
  *Colour:* Yellowish, Plate 13 near D.
Ovaries: All enclosed in calyx.
Sepals:
  1. Curl back when the bud develops.
  2. *Colour:*
    a. inside pale green, Plate 134D, with woolly hairs and a small blotch of pink — Plate 50C—in the centre.
    b. outside green—Plate 134, nearest to C.
Calyx: Cup-shaped, green—Plate 130 between A and B.

PLANT

Foliage:
  a. *Quantity:* The plant has abundant foliage—Leaves—compound of 5–7 leaflets.
  b. *Colour of foliage:*
    *New foliage:* Reddish-purple—Plate 184A.
    *Mature foliage:* Upper surface rich green—Plate 189A with a glossy surface and fine veined, reverse side flat, green—Plate 191B—and ribbed.

Shape: Oval, pointed at apex.

Margin: Singly serrated.

Serrates: Sharp-pointed, singly serrated.

Leaf stems (supporting stem of compound leaf): Medium caliper, covered with tiny hairy green thorns—Plate 138B—tinted reddish on surface side—Plate 185B.

Auricles: Small.

Disease resistance: Above average disease resistant as compared with other rose varieties.

Thorns: The thorns are of medium size and hooked downwards.

Colour of thorns: Reddish—Plate 184C.

Growth: Bushy, upright, well branched.

Habit: Vigorous.

COMPARISON WITH OTHER KNOWN WHITE ROSES

It differs from the variety White Christmas in colour. The old variety is a creamy white—Plate 155A—and the new variety is ivory white to snow white nearest to Plate 155D. In size the bud and flower of the new variety in comparison with the Pollen variety Pascali, U.S. Plant Pat. No. 2,592 is much larger, and the flower lasts longer on the plant and also in the vase.

I claim:

1. A new and distinct variety of rose plant of the hybrid tea class, substantially as herein described and shown, characterized particularly as to novelty by the unique combination of a vigorous growing plant with disease resisting foliage and exceptionally free flowering nature and the production of well formed extra large scented flowers, with perfect pointed buds borne on long rigid stems which hold the flowers upright, said flowers having the ability to retain their color and beauty in hot sun as well as in rainy weather.

No references cited.

ROBERT E. BAGWILL, Primary Examiner